United States Patent
Wu et al.

(10) Patent No.: US 11,474,180 B2
(45) Date of Patent: Oct. 18, 2022

(54) METHOD FOR OPTIMIZING T1-WEIGHTED MAGNETIC RESONANCE IMAGING OF INFANT BRAIN

(71) Applicant: ZHEJIANG UNIVERSITY, Hangzhou (CN)

(72) Inventors: Dan Wu, Hangzhou (CN); Yi Zhang, Hangzhou (CN); Tingting Liu, Hangzhou (CN); Hongxi Zhang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 37 days.

(21) Appl. No.: 17/218,172

(22) Filed: Mar. 31, 2021

(65) Prior Publication Data

US 2021/0215781 A1    Jul. 15, 2021

Related U.S. Application Data

(63) Continuation of application No. PCT/CN2020/089882, filed on May 12, 2020.

(51) Int. Cl.
*G01R 33/56* (2006.01)
*A61B 5/00* (2006.01)
*A61B 5/055* (2006.01)

(52) U.S. Cl.
CPC ........ *G01R 33/5602* (2013.01); *A61B 5/0042* (2013.01); *A61B 5/055* (2013.01)

(58) Field of Classification Search
CPC .... G01R 33/5602; A61B 5/0042; A61B 5/055
See application file for complete search history.

(56) References Cited

U.S. PATENT DOCUMENTS 10,444,311 B2 * 10/2019 Wang ............... A61B 5/004
10,617,343 B2 * 4/2020 Yarnykh ............. A61N 1/40
(Continued)

FOREIGN PATENT DOCUMENTS

CN    104161517 A    11/2014
CN    106127792 A    11/2016
(Continued)

OTHER PUBLICATIONS

International Search Report (PCT/CN2020/089882); dated Jul. 29, 2020.
(Continued)

*Primary Examiner* — Dixomara Vargas
(74) *Attorney, Agent, or Firm* — W&G Law Group (57) ABSTRACT

The present disclosure provides a method for optimizing T1-weighted magnetic resonance imaging of infant brains. Firstly, T1 and PD maps of infant brains at 0-12 months old are collected to obtain average T1 and PD values of WM and GM of the infant brains, and infants are classified into three age groups according to the characteristics of WM and GM T1 values of the infant brains. Then, the theoretical signal strength of the WM and GM of the infant brains generated from a 3D T1-weighted imaging sequence is calculated through Bloch simulation, and a theoretical optimal TI scheme of each group is determined according to the simulated WM/GM contrast characteristics under different TIs. Finally, the theoretical optimal TI scheme is applied to a target infant brain according to the designated age group for 3D T1-weighted magnetic resonance imaging.

6 Claims, 5 Drawing Sheets

(56) References Cited

U.S. PATENT DOCUMENTS

| | | | | |
|---|---|---|---|---|
| 2008/0292194 | A1* | 11/2008 | Schmidt | G06T 7/143 382/131 |
| 2010/0103166 | A1* | 4/2010 | Warntjes | A61B 5/055 345/617 |
| 2010/0260396 | A1* | 10/2010 | Brandt | G06T 7/174 382/131 |
| 2011/0004092 | A1* | 1/2011 | Kato | A61B 5/107 600/410 |
| 2012/0197105 | A1* | 8/2012 | Mezer | G01R 33/50 600/410 |
| 2015/0071514 | A1* | 3/2015 | Wang | G01R 33/543 382/131 |
| 2015/0073258 | A1* | 3/2015 | Mazer | G01R 33/50 600/410 |
| 2015/0302599 | A1* | 10/2015 | Crainiceanu | G06T 7/143 382/131 |
| 2016/0000945 | A1* | 1/2016 | Nedergaard | A61B 5/055 604/9 |
| 2017/0018080 | A1* | 1/2017 | Yokosawa | G06T 7/0012 |
| 2018/0064365 | A1 | 3/2018 | Srinivasan | |
| 2018/0268942 | A1* | 9/2018 | Kamali-Zare | G01R 33/5608 |
| 2019/0324102 | A1* | 10/2019 | Hernando | G01R 33/5608 |
| 2019/0365273 | A1* | 12/2019 | Jara | G01R 33/5602 |
| 2020/0341092 | A1* | 10/2020 | Jiang | G01R 33/50 |
| 2020/0408863 | A1* | 12/2020 | Liang | G01R 33/5615 |
| 2021/0312626 | A1* | 10/2021 | Griswold | G01R 33/5608 |
| 2021/0361167 | A1* | 11/2021 | Wolfe | A61B 5/7246 |

FOREIGN PATENT DOCUMENTS

| | | |
|---|---|---|
| CN | 106600621 A | 4/2017 |
| CN | 108171711 A | 6/2018 |
| CN | 109741319 A | 5/2019 |
| CN | 110123324 A | 8/2019 |
| WO | 2011015865 A1 | 2/2011 |

OTHER PUBLICATIONS

"Application of MRI T1 weighted inversion recovery sequence in evaluation of brain development in infants" (Aug. 31, 2015) [pp. 476-479].

"Automatic segmentation of infant brain MR images: With special reference to myelinated white matter" (Jan. 21, 2017) [pp. 143-156].

"MR Imaging Study on Normal Neonatal and Infant Brain Maturation" (Aug. 28, 2000) [pp. 147-149].

* cited by examiner

METHOD FOR OPTIMIZING T1-WEIGHTED MAGNETIC RESONANCE IMAGING OF INFANT BRAIN

TECHNICAL FIELD

The present disclosure relates to the field of brain magnetic resonance imaging optimization, and in particular, to optimization of infant brain T1-weighted imaging.

BACKGROUND

Infant brain magnetic resonance imaging (MRI) is a safe and widely used method for examining structures and functions of infant brains and neurological diseases in early development. However, due to the poor contrast of infant brain MRI and the rapid change of image contrast caused by rapid brain development in the first year of life, it is difficult to perform anatomical segmentation and automatic image analysis on the infant brain images. The contrast between gray matter (GM) and white matter (WM) in a T1-weighted (T1w) image of a neonatal (less than or equal to 1 month) brain is opposite to that of an adult brain due to the prolonged T1 relaxation time caused by immature myelination of WM at birth. The contrast of older infants is similar to that of adults, and the reversal is preceded by a period in which WM and GM signal intensities are similar, which is typically in 3-6 months after birth.

At present, some studies have worked on the optimization of T1w imaging of neonatal brains. However, in fact, the neonatal brain WM/GM contrast remained poor; theoretically, the highest neonatal WM/GM contrast can only reach ⅓ of that of the adults at 3T. Moreover, the WM/GM contrast in rest of the infant period (1-12 months old) is even worse and more complex than that in the first month after birth, and there are few studies on brain optimization imaging in infants 1-12 months old currently.

It is worth mentioning that since WM and GM signals in brains of infants around 6 months old are almost identical, it is still a great challenge to segment brain images of infants in this period. Some studies improved segmentation results to some extent by extending the scanning time, integrating multimodal data, and deep learning methods. In addition to the development of advanced image processing algorithms, improving the image contrast in an acquisition process is of great benefit to the subsequent analysis.

SUMMARY

In order to break the blank of optimization of T1w imaging during the whole infant period (0-12 months), the present disclosure provides a method for optimizing T1w MRI of the infant brains. In this method, firstly, brain T1 and proton density (PD) maps of infants 0-12 months old are collected to obtain regionally averaged T1 relaxation time and PD values in WM and GM of the infant brains, and infants are grouped into different month age bins according to the development-dependent patterns of WM T1 values and GM T1 values in the infant brains. Next, WM and GM signals under different inversion times (TIs) are calculated by Bloch simulation. Then, a theoretical optimal TI optimization scheme for each month age group is determined. Finally, the theoretical optimal TI optimization scheme is applied to a 3D T1w MRI sequence. The present disclosure fills the blank of brain T1-weighted imaging optimization during the whole infant period, and groups infants into three age groups according to relationship characteristics of T1 values of WM and GM of infant brains, and finds out optimal TI optimization schemes for different month age groups respectively, so as to significantly improve the T1-weighted imaging contrast of the infant brains. The realization of this method is beneficial to the anatomical segmentation of infant brains and the detection of diseases, and the method is simple and convenient to be applied to clinical routine examination.

In order to achieve the above objective, the present disclosure adopts the following technical solutions for implementation:

A method for optimizing T1-weighted magnetic resonance imaging of infant brains, including steps of:

S1: collecting T1 and PD maps of brains of a number of infants at different ages from 0 to 12 months old respectively as subjects, to obtain regionally averaged T1 values and PD values in brain WM and GM regions of each of the infant brain;

S2: grouping the infants into three age groups according to the relative relationship of T1 values between WM and GM of the infant brains;

S3: calculating, through Bloch simulation according to the average T1 value and the average PD value of the brain WM and GM regions of the infant brains in different age groups, a theoretical signal strength in the WM and GM of the infant brain acquired from a 3D T1-weighted MPRAGE sequence; and determining a theoretical optimal TI scheme for each age group respectively to maximize contrast between WM and GM; and S4: performing 3D T1-weighted magnetic resonance imaging on a target infant brain using the theoretical optimal TI scheme.

Based on the solution, the steps may further provide the following preferred implementation modes. It should be noted that the technical features in each preferred manner can be combined with each other without conflict. Of course, the preferred manners can also be implemented in other ways that can achieve the same technical effect, and they do not constitute limitations.

Preferably, a method for calculating the regionally averaged T1 values and PD values in step S1 includes steps of:

S101: collecting T1 and PD maps of a number of infant brains at different ages from 0 to 12 months old respectively;

S102: delineating regions of interest of cortical GM and subcortical WM; and

S103: for each infant brain, calculating an average T1 value of the subcortical WM voxels as an average T1 value of the brain WM; calculating an average PD value of the subcortical WM voxels as an average PD value of the brain WM; calculating an average T1 value of the cortical GM voxels as an average T1 value of the brain GM; and calculating an average PD value of the cortical GM voxels as an average PD value of the brain GM.

Preferably, a method for grouping the infants into three age groups in step S2 includes steps of:

grouping the infants into three age groups according to the relative relationship of T1 values between WM and GM of the infant brains at different ages, wherein the relationship of the three groups are respectively as follows:

in the first age group, the brain WM T1 value of each infant is higher than the brain GM T1 value of the infant;

in the second age group, the brain WM T1 value of each infant is close to the brain GM T1 value of the infant; and in the third age group, the brain WM T1 value of each infant is lower than the brain GM T1 value of the infant.

Preferably, the three age groups are 0-3 months old (i.e., 0-90 days after birth), 3-7 months old (91-210 days after birth) and 7-12 months old (211-360 days after birth), respectively.

Preferably, a method for determining the theoretical optimal TI scheme in step S3 includes steps of:

S301: for the average T1 value and the average PD value of the WM and GM regions of the infant brains in each age group, simulating the 3D T1-weighted MPRAGE sequence by Bloch equation; during the simulation, fixing an inversion pulse α, the number of excitation pulses N, an excitation pulse flip angle θ, an echo interval τ and delay time TD in the MPRAGE sequence, and changing inversion time TI; and calculating a signal strength $s_1$ of a first readout pulse in voxel as:

$$s_1 = M_0 \cdot \left((1-\lambda) - \lambda \cdot \frac{M_{eq}}{M_0}\right) \cdot \sin\theta$$

where $$M_{eq} = \frac{1 - \varphi + \frac{\varphi \cdot \cos\theta \cdot (1-\delta) \cdot (1-\mu^{N-1})}{1-\mu} + \varphi \cdot \cos\theta \cdot \mu^{N-1} + \rho \cdot \cos\alpha \cdot \cos^N(\theta)}{1 - \rho \cdot \cos\alpha \cdot \cos^N(\theta)} M_0$$

in the equation, $M_0$ is an initial magnetization, N is the number of single excitations in a slice encoding direction, $$\lambda = e^{-\frac{TI}{T1}}, \varphi = e^{-\frac{TD}{T1}}, \delta = e^{-\frac{\tau}{T1}}, \rho = e^{-\frac{TR}{T1}}, \mu = \delta \cdot \cos\theta;$$

is a to-be-calculated average T1 value of brain WM or brain GM of all subjects in an age group; TR=T1+N·τ+TD;

S302: calculating an image contrast under different TIs respectively for different age groups determined in S2, wherein an absolute contrast=$|S_{WM}|-|S_{GM}|$; a relative contrast=$(|S_{WM}|-|S_{GM}|)/(|S_{WM}|+|S_{GM}|)$;

in the equation, $S_{WM}$ is an average signal strength of WM voxels calculated according to the formula in S301, and $S_{GM}$ is an average signal strength of GM voxels calculated according to the formula in S301; and S303: determining a theoretical optimal TI scheme for each age group respectively according to the image contrast of different age groups under different TIs, wherein for the first and third age groups, the image contrasts under different TIs with fixed θ and TR are compared, and corresponding TIs when the relative contrast of each group is the highest and the absolute contrast is relatively high are determined respectively; and for the second age group, two different TI images with the highest but opposite relative contrasts are collected using two TIs on both sides of a TI inversion point, and the image contrast is enhanced by subtraction between the two groups of images.

Preferably, the theoretical optimal TI scheme in step S4 includes:

setting 3D T1-weighted magnetic resonance imaging parameters as θ=10° and TR=2000 ms;

classifying the 0-3 months old into the first group, and setting TI to 700-800 ms during the 3D T1-weighted MRI scans;

classifying the 3-7 months old into the second group, setting TIs to 500 ms and 700 ms respectively during the 3D T1-weighted MRI scans, and obtaining images with optimized contrasts by subtraction between the images obtained under TIs of the two groups; and classifying the 7-12 months old into the third group, and setting TI to 600-700 ms during the 3D T1-weighted MRI scans.

Another objective of the present disclosure is to provide a method for optimizing T1-weighted magnetic resonance imaging of infant brains for practical use, including the following specific steps:

1) selecting a corresponding optimal TI scheme according to the current age of an infant: if the age is 0-3 months old (i.e. 0-90 days after birth), setting TI to 700-800 ms in the 3D T1-weighted MPRAGE sequence; if the age is 3-7 months old (i.e. 91-210 days after birth), setting TIs to 400-500 ms and 600-700 ms respectively in the 3D T1-weighted MPRAGE sequence to acquire two images, and subtracting the images obtained under different TIs to obtain images with optimized contrast; and if the age is 7-12 months old (i.e. 211-360 days after birth), setting in the 3D T1-weighted MPRAGE sequence; and 2) setting other parameters as θ=10° and TR=2000 ms, and then performing the 3D T1-weighted MPRAGE on a target infant brain according to the determined parameters, to complete the optimized acquisition.

Compared with the existing technology, the present disclosure has the following characteristics: the present disclosure realizes the optimization of brain T1w imaging during the whole infant period for the first time. Firstly, the present disclosure classifies the infant period into three age groups according to relative relationship of T1 values between WM and GM of infant brains during development, and focuses on realizing the imaging optimization of infant brains at different ages by changing TI. The method has the advantages of easy implementation, short acquisition time and high isotropic resolution, and is suitable for routine clinical scanning.

Secondly, for the brains of infants 3-6 months old with the worst contrast, the present disclosure provides a double TIs scanning method, that is, two images with opposite contrast are collected using two TIs on both sides of a TI inversion point, and the image contrast is enhanced by subtracting the two images.

Next, the present disclosure uses RC as a main evaluation criterion for image contrast, rather than AC or AC derivatives used in other methods. As can be seen from the definition, the size of AC depends on the signal strength of the image itself, while RC can more truthfully reflect the contrast of the image.

Finally, the present disclosure uses a centric phase-encoding scheme for MRI acquisition rather than nonlinear encoding. Since the T1w contrast generated by linear phase encoding depends on the number of steps in the phase encoding and the local Fourier coefficients, its generalizability is worse than centric encoding.

DESCRIPTION OF EMBODIMENTS

The specific technical effect thereof is demonstrated below based on the method provided in the present disclosure in combination with embodiments, so that those skilled in the art can better understand the essence of the present disclosure.

Figure 1:
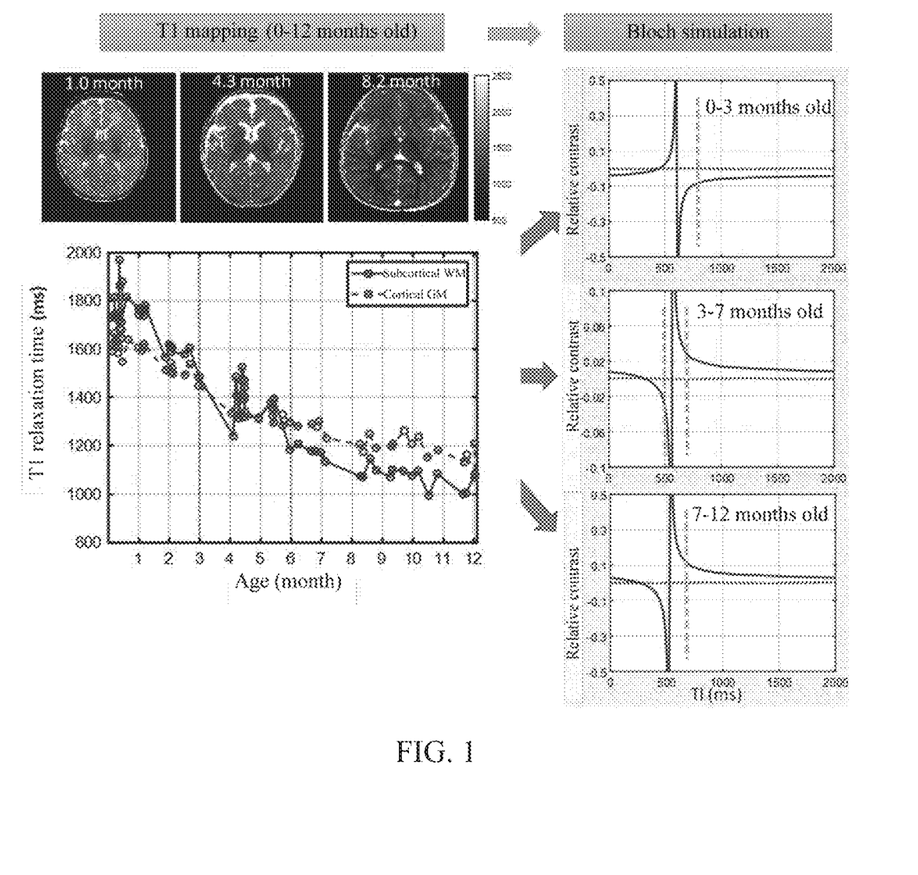
FIG. 1 is the flowchart of a method for optimizing T1w magnetic resonance imaging of infant brains.

In a preferred implementation mode of the present disclosure, as shown in FIG. 1, a method for optimizing T1-weighted magnetic resonance imaging of infant brains includes the following steps:

S1: T1 and PD maps of brains of multiple infants at different ages from 0 to 12 months old are collected as subjects on a 3T MRI scanner. The subjects need to exclude subjects with any known changes in the Tw contrast or abnormalities found on MRI images. The subjects should be distributed as evenly as possible at different ages from 0 to 12 months old. Then, regionally averaged T1 relaxation times and PD values in white matter (WM) and gray matter (GM) regions of each infant brain are calculated. A specific calculation method is as follows:

Firstly, regions of interest (ROIs) of cortical GM and subcortical WM are delineated in sample images. Then, for each infant brain, an average T1 value of the subcortical WM is calculated as an average T1 value of the WM of the infant brain; an average PD value of the subcortical WM is calculated as an average PD value of the WM of the infant brain; an average T1 value of the cortical GM is calculated as an average T1 value of the GM of the infant brain; and an average PD value of the cortical GM is calculated as an average PD value of the GM of the infant brain.

S2: the infants are grouped into three age groups according to relative relationship of T1 values between WM and GM of the infant brains during development. Rapid brain development in the first year of life leads to rapid changes in image contrast. With the continuous development of infant brains, relationships between T1 values of brain WM and GM in infants in different age stages may demonstrate different characteristics, and the different relationship of T1 values between brain WM and GM determines the final imaging contrast, so it is necessary to perform group-specific optimization. In the present disclosure, infants may be grouped into three month age groups according to different relationship. Relationship between WM and GM T1 values in the three groups are as follows.

in the first age group, the brain WM T1 value of the infant is higher than the brain GM T1 value of the infant;

in the second age group, the brain WM T1 value of the infant is close to the brain GM T1 value of the infant; and in the third age group, the brain WM T1 value of the infant is lower than the brain GM T1 value of the infant.

According to subsequent embodiments, a preferred definition of the three age groups in the present disclosure is:

grouping infants 0-90 days old after birth into the first group, that is, 0-3 months old;

grouping infants 91-210 days old after birth into the second group, that is, 3-7 months old; and grouping infants 211-360 days old after birth into the third group, that is, 7-12 months old.

Due to the different MRI features of the infant brains in the above three age groups, the corresponding optimal TI optimization should be performed for the three groups respectively, so as to effectively improve the T1-weighted imaging contrast of infant brains in each age group.

After the group assignment, the regional average T1 relaxation times and PD values in brain WM and GM regions in each month age group should be averaged across subjects within the age group to serve as average T1 and PD values of the brain WM and GM regions of this month age group. For any month age group, the average WM T1 value of the infant brains in the age group is an arithmetic mean of infant brain WM average T1 values of all the subjects in the age group; the average WM PD value of the infant brains in the age group is an arithmetic mean of infant brain WM average PD values of all the subjects in the age group; the average GM T1 value of the infant brains in the age group is an arithmetic mean of infant brain GM average T1 values of all the subjects in the age group; and the average GM PD value of the infant brains in the age group is an arithmetic mean of infant brain GM average PD values of all the subjects in the age group.

S3: theoretical signal strength of the WM and GM regions of the infant from a 3D T1-weighted MPRAGE sequence is calculated through Bloch simulation according to the group averaged T1 values and PD values of the brain WM and GM regions of the infant brains in each age group; and a theoretical optimal TI scheme for each age group is determined respectively according to the simulated contrasts between WM and GM. Herein, a specific method for determining the theoretical optimal TI scheme is as follows:

S301: for the average T1 value and the average PD value in each month age group, the 3D T1-weighted MPRAGE sequence is simulated according to the Bloch equation; during the simulation, an inversion pulse flip angle α, the number of excitation pulses N, an excitation pulse flip angle θ, an echo interval τ and delay time TD in the MPRAGE sequence are fixed, and inversion time TI is changed to calculate signal strength under different TIs. The image contrast is determined by the first readout signal.

a transverse signal of the $i^{th}$ readout pulse is $$s_i = M_0 \cdot \left( \frac{(1-\delta) \cdot (1-\mu^{i-1})}{1-\mu} + \mu^{i-1} \cdot (1-\lambda) - \lambda \cdot \mu^{i-1} \cdot \frac{M_{eq}}{M_0} \right) \cdot \sin\theta \qquad \text{Equation (1)}$$

where the parameter $M_{eq}$ is:

$$M_{eq} = \frac{1 - \varphi + \frac{\varphi \cdot \cos\theta \cdot (1-\delta) \cdot (1-\mu^{N-1})}{1-\mu} + \varphi \cdot \cos\theta \cdot \mu^{N-1} + \rho \cdot \cos\alpha \cdot \cos^N(\theta)}{1 - \rho \cdot \cos\alpha \cdot \cos^N(\theta)} \cdot M_0 \qquad \text{Equation (2)}$$

in the equation, $M_0$ is an initial magnetization vector ($M_0$ is relevant to the calculated average PD value of WM and GM), and N is the number of single excitations in a slice encoding direction; λ, 100, δ, ρ and μ are all intermediate parameters, $$\lambda = e^{-\frac{TI}{T1}}, \varphi = e^{-\frac{TD}{T1}}, \delta = e^{-\frac{\tau}{T1}}, \rho = e^{-\frac{TR}{T1}}, \mu = \delta \cdot \cos\theta,$$

and the total repetition time TR=TI+N·τ+TD. T1 is the average T1 value of brain WM or brain GM of infant brains in an age group (determined according to the method described in S2).

Spatial encoding uses a centric phase-encoding method and the image contrast is determined by the first readout signal. Thus, the Equation (1) may be simplified as Equation (3), and the signal strength $s_1$ of the first readout pulse in a voxel is calculated as:

$$s_1 = M_0 \cdot \left((1-\lambda) - \lambda \cdot \frac{M_{eq}}{M_0}\right) \cdot \sin\theta \qquad \text{Equation (3)}$$

It should be noted that in the calculation of equation (3) above, values of T1 are different when different signal values are calculated. Specifically, for any month age group, when an average WM voxel signal $S_{WM}$ of the age group is calculated, the value of T1 is the average T1 value of brain WM of the infant brains in the age group, and $S_{WM}$ is the signal intensity $s_1$ calculated according to the Equation (3) at this time; when an average GM voxel signal $S_{GM}$ of the age group is calculated, the value of T1 is the average T1 value of brain GM of the infant brains in the age group, and $S_{GM}$ is the signal intensity $s_1$ calculated according to the Equation (3) at this time.

S302: for different age groups set in S2, the image contrast under different TIs is calculated respectively, and the image contrast is defined by absolute contrast and relative contrast.

The absolute contrast(AC)=$|S_{WM}-S_{GM}|$

The relative contrast(RC)=$(|S_{WM}|-|S_{GM}|)/(|S_{WM}|+|S_{GM}|)$

S303: according to the image contrast of different age groups under different TIs, the WM/GM contrast is taken as a standard to determine the theoretical optimal TI optimization scheme for each month age group. As RC is less affected by the signal strength of the image itself than AC, RC is taken as a primary evaluation standard in the present disclosure. On the other hand, since AC is related to a signal-to-noise ratio, AC is taken as an auxiliary evaluation standard.

Specific determination methods are different for the three age groups:

For the first age group and the third age group, compare the image contrasts under different TIs with fixed θ and TR, and determine the corresponding TIs when the RC of each group is the highest and the AC is relatively high. Herein, the AC being relatively high means that the AC may not be the highest, but should be greater than a certain threshold (the threshold may be set according to actual needs).

For the second age group, since brain WM and GM signals are close, two different TI images with the highest RC and opposite WM/GM contrast performance are acquired using two TIs on both sides of a TI inversion point, and the image contrast is enhanced by subtraction between the two images.

According to subsequent embodiments, a preferred manner of the theoretical optimal TI optimization scheme finally determined for the three age groups in the present disclosure is.

setting 3D T1-weighted MRI parameters as θ=10° and TR=2000 ms;

grouping 0-3 months old (i.e. 0-90 days after birth) into the first group, and setting TI to 700-800 ms during the 3D T1-weighted MRI scans;

grouping 3-7 months old (i.e. 91-210 days after birth) into the second group, setting TIs to 400-500 ms and 600-700 ms respectively during the 3D T1-weighted MRI scans, and subtracting the two images obtained under different TIs (subtracting the image obtained from TI=400-500 ms from the image obtained from TI=600-700 ms, i.e. $TI_{600-700\ ms}-TI_{400-500\ ms}$) to obtain images with optimized contrast; and grouping 7-12 months old (i.e. 211-360 days after birth) into the third group, and setting TI to 600 to 700 ms during the 3D T1-weighted MRI scans.

S4: 3D T1-weighted MRI is performed on a target infant brain using the theoretical optimal TI scheme.

The technical effect thereof is demonstrated below based on the above method in combination with embodiments, so that those skilled in the art can better understand the essence of the present disclosure.

Embodiment

The method for optimizing T1-weighted MRI of infant brains is tested. Firstly, sequential images acquired with the "MIX" sequence of 57 normally developing infants are collected using a Philips 3T MRI scanner (Achieva; Philips Healthcare, Best, The Netherlands), spin echo (SE) and inversion Recovery (IR) signal equations are solved based on a ratio and least square algorithm to obtain T1 and PD maps respectively, and the PD values in the lateral ventricle is used as a standard to normalize PD values of the brains.

Regions of interest (ROI) are manually delineated on T1 Maps, including cortical GM and subcortical WM. For each infant brain, an average T1 value of the subcortical WM is calculated as an average T1 value in the WM of the infant brain; an average PD value of the subcortical WM is calculated as an average PD value in the WM of the infant brain; an average T1 value of the cortical GM is calculated as an average T1 value in the GM of the infant brain; and an average PD value of the cortical GM is calculated as an average PD value in the GM of the infant brain.

Figure 2:
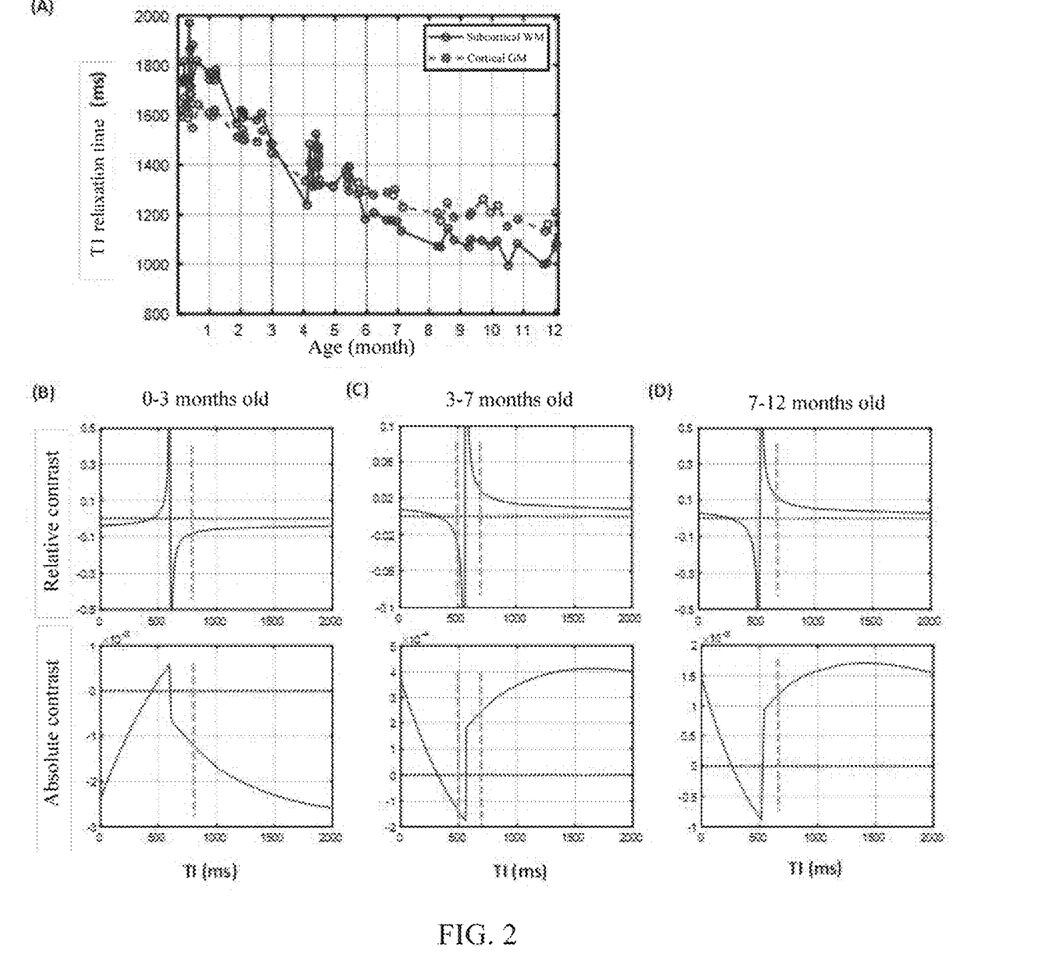
FIG. 2 shows calculation of WM and GM T1 relaxation time and WM/GM contrast of infant brains at 3 months old by Bloch simulation.

T1 measurements (FIG. 2A) show that the T1 value of the subcortical WM was higher than that of the cortical GM before 3 months old; the T1 values of WM and GM were close in 3-7 months; and after 6 months old, the T1 value of WM was lower than that of GM. On the basis of this pattern, infants can be grouped into a group of 0-3 months old (i.e. 0-90 days after birth), a group of 3-7 months old (i.e. 91-210 days after birth) and a group of 7-12 months old (i.e. 211-360 days after birth). An average T1 value and an average PD value of brain WM and GM regions in all subjects in each age group are averaged mathematically, average T1 and PD values of the brain WM and GM regions of the infant brains in each age group are calculated, and theoretical signal strength of the WM and GM of the infant brains in age group is calculated by Bloch simulation. The results are as follows:

1) WM/GM contrast inversion occurs in the infant brains in the group of 0-3 months old at TI=602 ms (FIG. 2B), and positive and negative contrasts take place on two sides of the inversion point. The contrast is close to zero at the inversion point, due to the very close WM and GM signals at the inversion point. Therefore, the selection of the optimal T1 should not only pursue high RC, but also take AC (reflecting the signal-to-noise ratio) into consideration. For example, when TI=800 ms (the vertical dotted line in FIG. 2B), RC is about −0.1, and AC is about half of the maximum AC in the 0-3 months old.

2) Because the T1 relaxation time of WM and GM of the brains of the infants in the group of 3-7 months old is highly similar (1342±104 ms and 1354±55 ms), RC and AC are both lower in this group than in the other groups (FIG. 2C, note that the y-axis ratio is different from that in FIG. 2B and FIG. 2D). For this stage, images at dual TIs are selected to be acquired on both sides of the contrast inversion point. For example, two images with opposite contrasts and high RC and AC can be obtained at TI=500 ms and 700 ms. By subtracting the two images, the difference between WM and GM can be enhanced.

3) RC and AC curves of the infant brains in 7-12 months old group (FIG. 2D) are opposite to those of the 0-3 months old group (FIG. 2B), and the contrast inversion point moves towards lower TI with brain development. Similarly, RC and AC should be considered at the same time in the selection of the optimal TI. For example, when TI=700 ms, RC is about 0.1, and AC is about ⅔ of the maximum AC in the 7-12 months old group.

A set of 3D MPRAGE images of the infant brains between 0-12 months old are additionally collected, with a field of view is 180 mm×180 mm×120 mm, slice selection in the axial direction, a matrix of 180×180×120, TR/TE=2000/3.7 ms, τ=8 ms, spatial encoding using a centric phase-encoding method, α=180°, θ=10°, N=120 (the number of single excitations in the slice encoding direction), SENSE acceleration factor of 2 (acceleration in the phase encoding direction), and the scan time of 3.07 minutes. Based on Bloch simulation results (FIG. 2), the following are tested respectively: 1) TI is set to 500, 700, 800 and 1000 ms to scan six full-term neonatal brains respectively; 2) TI is set to 500 and 700 ms to scan seven 3-7 months old infant brains respectively; and 3) TI is set to 700, 800 and 1000 ms to scan five 7-12 months old infant brains respectively.

Figure 3:
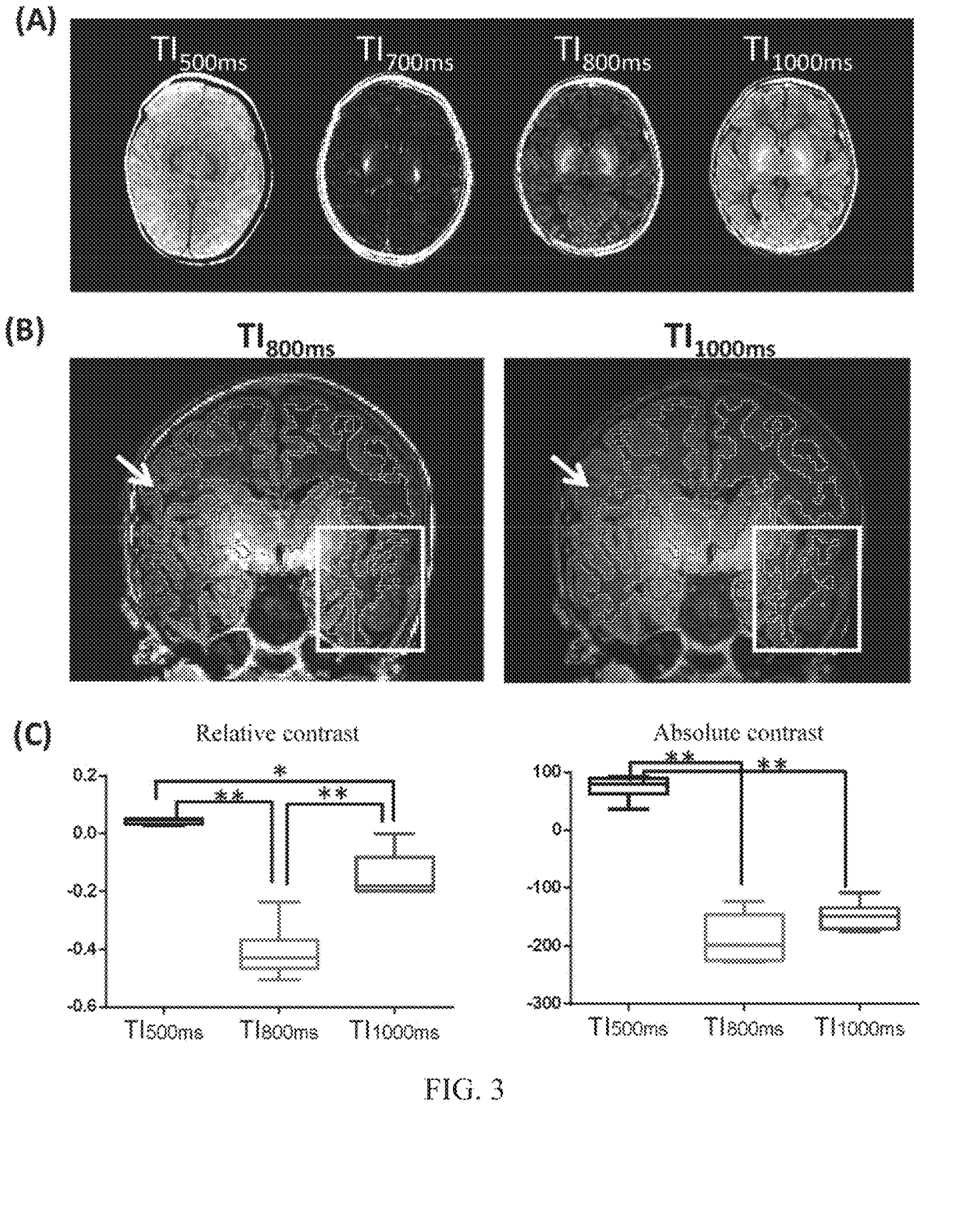
FIG. 3 shows optimization results of 3D T1w imaging for neonatal brains.

FIG. 3A shows that the T1w image contrast in neonatal brains may change within the range of TI=500 ms to TI=1000 ms. For example, $TI_{500\ ms}$ shows low positive contrast ($S_{WM}>S_{GM}$), $TI_{700\ ms}$ shows a low signal-to-noise ratio, $TI_{800\ ms}$ and $TI_{1000\ ms}$ show medium negative contrast ($S_{WM}<S_{GM}$), which is consistent with the simulation results. Multi-atlas based image segmentation is performed on $TI_{800\ ms}$ and $TI_{1000\ ms}$. It can be found visually that the segmentation accuracy of the $TI_{800\ ms}$ image is higher than that of $TI_{1000\ ms}$, especially for the segmentation between subcortical WM and cortical GM (arrows and boxes in FIG. 3B). Based on the segmentation of GM and WM on $TI_{800\ ms}$ images, RC and AC of $TI_{1000\ ms}$, $TI_{800\ ms}$ and $TI_{1000\ ms}$ images show statistical differences. The Post-hoc t test confirms that RC of $TI_{800\ ms}$ is higher than that of the $TI_{1000\ ms}$ image ($p<0.001$, $n=6$), while AC shows no statistical difference (FIG. 3C).

Figure 4:
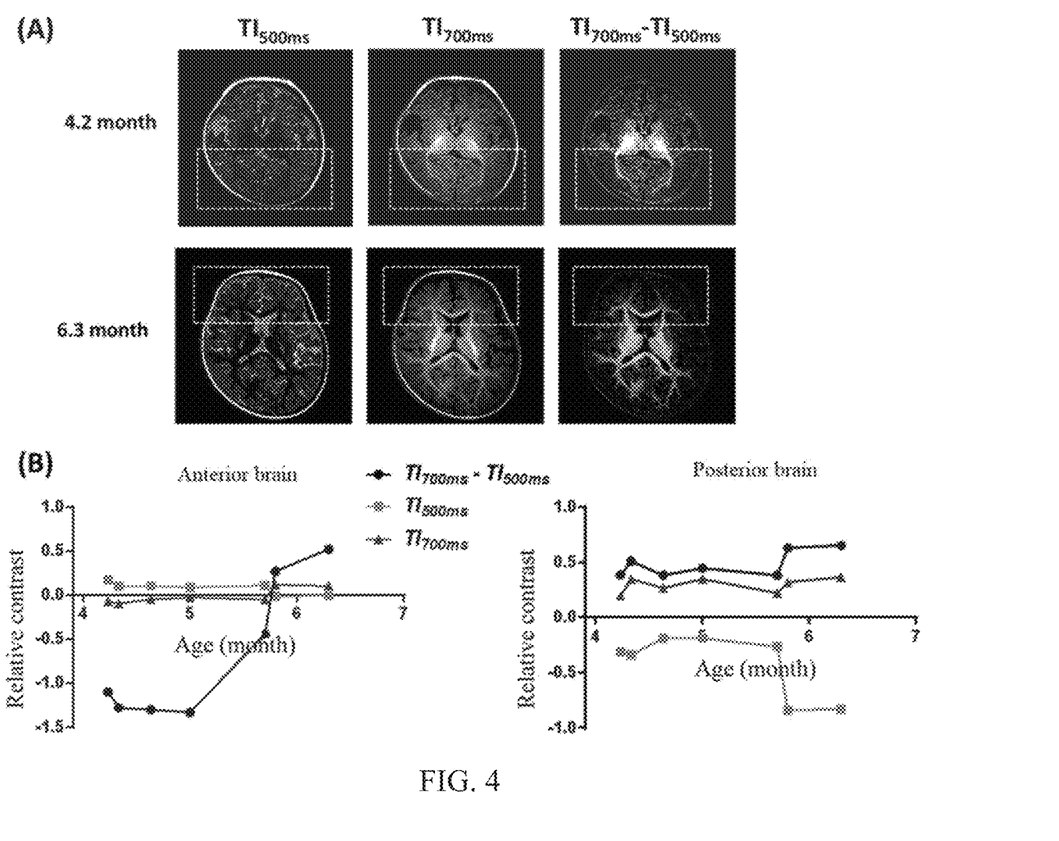
FIG. 4 shows optimization results of 3D T1w imaging for infant brains at 3-7 months old.

In the group of infants 3-7 months old, the contrast of the $TI_{500\ ms}$ image is opposite to that of the $TI_{700\ ms}$ image, and the image contrast can be enhanced by image subtraction ($TI_{700\ ms}-TI_{500\ ms}$), which is also consistent with the simulation results. FIG. 4 shows that RC of the anterior brain is low and the contrast is inverted during 5.7-5.8 months, while RC of the posterior brain is low but presents positive contrast and increases after 5.7 months. Compared with the TI image acquired at a single TI, the WM/GM contrast can be enhanced by image subtraction ($TI_{700\ ms}-TI_{500\ ms}$).

Figure 5:
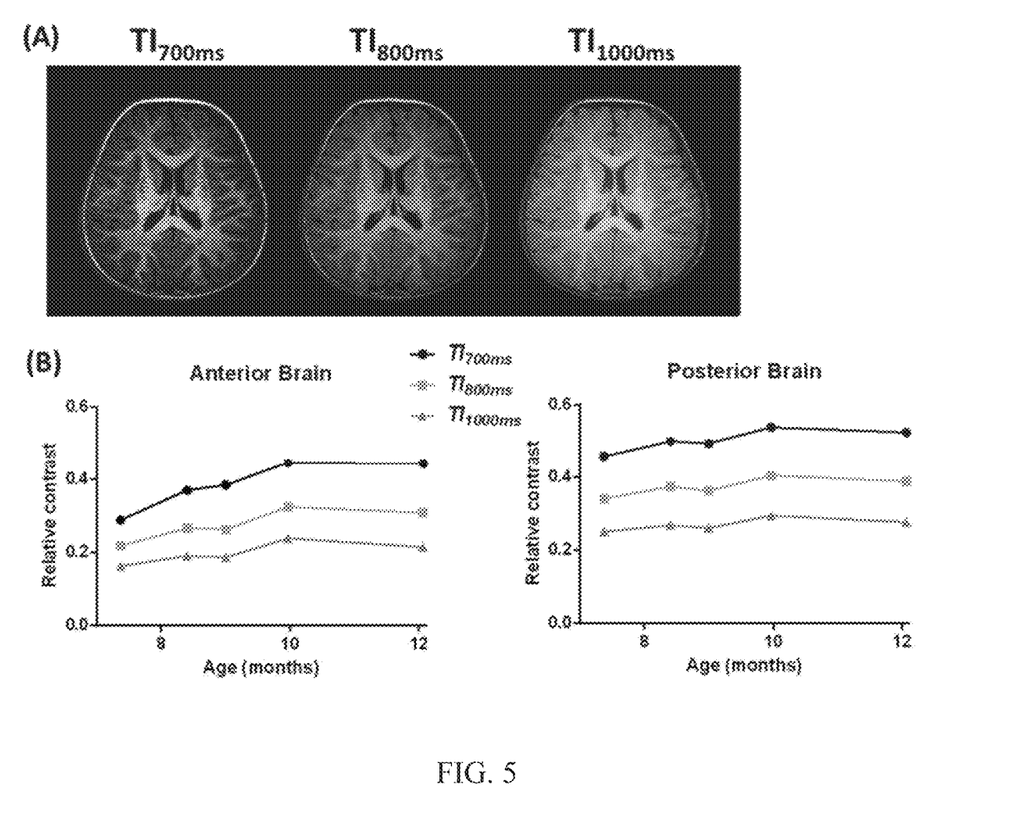
FIG. 5 shows optimization results of 3D T1w imaging for infant brains at 7-12 months old.

For infants 7-12 months old, the T1w image contrast is close to that of adults and significantly higher than that of the other two groups. TIs of 700, 800 and 1000 ms were tested for this group. Similarly, the image contrast is calculated by delineating the ROIs of anterior and posterior cortical GM and subcortical WM. FIG. 5 shows that RC of the $TI_{700\ ms}$ image is higher than that of $TI_{800\ ms}$ and $TI_{1000\ ms}$, which is also consistent with the simulation results. Moreover, the contrasts in the anterior and posterior brain regions both increase with age.

To sum up, a method for optimizing T1-weighted MRI of infant brains can be provided based on the structural results in this embodiment, which is performed as follows:

selecting a corresponding theoretical optimal TI scheme according to the current age of an infant:

if the age is 0-3 months old (i.e. 0-90 days after birth), setting TI to 700-800 ms during 3D T1-weighted MRI; if the age is 3-7 months old (i.e. 91-210 days after birth), setting TIs to 500 ms and 700 ms respectively during the 3D T1-weighted MRI scans, and subtracting the images obtained under the two TIs ($TI_{700\ ms}-TI_{500\ ms}$) to obtain images with optimized contrast; and if the age is 7-12 months old (i.e. 211-360 days after birth), setting TI to 600-700 ms during the 3D T1-weighted MRI scans. Other parameters are set as θ=10° and TR=2000 ms during the 3D T1-weighted MRI scans, and then the 3D T1-weighted MRI is performed on a target infant brain according to the determined parameters, to complete the optimization.

It should be noted that, the embodiment described above is merely a preferred solution of the present disclosure, which is not intended to limit the present disclosure. Those of ordinary skill in the art can also make various changes and modifications without departing from the spirit and scope of the present disclosure. Therefore, all the technical solutions obtained by equivalent replacement or equivalent transformation fall within the protection scope of the present disclosure.

What is claimed is:

1. A method for optimizing T1-weighted magnetic resonance imaging of infant brains, comprising steps of:
    S1: collecting T1 and PD maps of brains of a number of infants at different ages from 0 to 12 months old respectively as subjects, to obtain regionally averaged T1 values and PD values in brain WM and GM regions of each of the infant brain;
    S2: grouping the infants into three age groups according to the relative relationship of T1 values between WM and GM of the infant brains;
    S3: calculating, through Bloch simulation according to the average T1 value and the average PD value of the brain WM and GM regions of the infant brains in different age groups, a theoretical signal strength in the WM and GM of the infant brain acquired from a 3D T1-weighted MPRAGE sequence; and determining a theoretical optimal TI scheme for each age group respectively to maximize contrast between WM and GM; and
    S4: performing 3D T1-weighted magnetic resonance imaging on a target infant brain using the theoretical optimal TI scheme.

2. The method for optimizing T1-weighted magnetic resonance imaging of infant brains according to claim 1, wherein a method for calculating the regionally averaged T1 values and PD values in step S1 comprises steps of:
    S101: collecting T1 and PD maps of a number of infant brains at different ages from 0 to 12 months old respectively;
    S102: delineating regions of interest of cortical GM and subcortical WM; and
    S103: for each infant brain, calculating an average T1 value of the subcortical WM voxels as an average T1 value of the brain WM; calculating an average PD value of the subcortical WM voxels as an average PD value of the brain WM; calculating an average T1 value of the cortical GM voxels as an average T1 value of the brain GM; and calculating an average PD value of the cortical GM voxels as an average PD value of the brain GM.

3. The method for optimizing T1-weighted magnetic resonance imaging of infant brains according to claim 1, wherein a method for grouping the infants into age groups in step S2 comprises steps of:
grouping the infants into three age groups according to the relative relationship of T1 values between WM and GM of the infant brains at different ages, wherein the relationship of the three groups are respectively as follows:
in the first age group, the brain WM T1 value of each infant is higher than the brain GM T1 value of the infant;
in the second age group, the brain WM T1 value of each infant is close to the brain GM T1 value of the infant; and
in the third age group, the brain WM T1 value of each infant is lower than the brain GM T1 value of the infant.

4. The method for optimizing T1-weighted magnetic resonance imaging of infant brains according to claim 1, wherein the three age groups are 0-3 months old, 3-7 months old and 7-12 months old respectively.

5. The method for optimizing T1-weighted magnetic resonance imaging of infant brains according to claim 4, wherein a method for determining the theoretical optimal TI scheme in step S3 comprises steps of:
S301: for the average T1 value and the average PD value of the WM and GM regions of the infant brains in each age group, simulating the 3D T1-weighted MPRAGE sequence by Bloch equation; during the simulation, fixing an inversion pulse α, the number of excitation pulses N, an excitation pulse flip angle θ, an echo interval τ and delay time TD in the MPRAGE sequence, and changing inversion time TI; and calculating a signal strength $s_1$ of a first readout pulse in voxel as:

$$s_1 = M_0 \cdot \left((1-\lambda) - \lambda \cdot \frac{M_{eq}}{M_0}\right) \cdot \sin\theta$$

where $$M_{eq} = \frac{1 - \varphi + \frac{\varphi \cdot \cos\theta \cdot (1-\delta) \cdot (1-\mu^{N-1})}{1-\mu} + \varphi \cdot \cos\theta \cdot \mu^{N-1} + \rho \cdot \cos\alpha \cdot \cos^N(\theta)}{1 - \rho \cdot \cos\alpha \cdot \cos^N(\theta)} M_0$$

in the equation, $M_0$ is an initial magnetization vector, N is the number of single excitations in a slice encoding direction, $$\lambda = e^{-\frac{TI}{T1}}, \varphi = e^{-\frac{TD}{T1}}, \delta = e^{-\frac{\tau}{T1}}, \rho = e^{-\frac{TR}{T1}}, \mu = \delta \cdot \cos\theta;$$

T1 is a to-be-calculated average T1 value of brain WM or brain GM of all subjects in an age group; TR=T1+N·τ+TD;
S302: calculating an image contrast under different TIs respectively for different age groups determined in S2, wherein an absolute contrast=$|S_{WM}|-|S_{GM}|$; a relative contrast=$(|S_{WM}|-|S_{GM}|)/(|S_{WM}|+|S_{GM}|)$;
in the equation, $S_{WM}$ is an average signal strength of WM voxels calculated according to the formula in S301, and $S_{GM}$ is an average signal strength of GM voxels calculated according to the formula in S301; and
S303: determining a theoretical optimal TI scheme for each age group respectively according to the image contrast of different age groups under different TIs, wherein
for the first and third age groups, the image contrasts under different TIs with fixed θ and TR are compared, and the corresponding TIs when the relative contrast of each group is the highest and the absolute contrast is relatively high are determined as the optimal TIs; and
for the second age group, two different TI images with the highest but opposite relative contrasts are collected using two TIs on both sides of a TI inversion point, and the image contrast is enhanced by subtraction between the two groups of images.

6. The method for optimizing T1-weighted magnetic resonance imaging of infant brains according to claim 1, wherein the theoretical optimal TI scheme in step S4 comprises:
setting 3D T1-weighted magnetic resonance imaging parameters as θ=10° and TR=2000 ms;
classifying the 0-3 months old into the first group, and setting TI to 700-800 ms during the 3D T1-weighted magnetic resonance imaging scans;
classifying the 3-7 months old into the second group, setting TIs to 500 ms and 700 ms respectively during the 3D T1-weighted magnetic resonance imaging scans, and obtaining images with optimized contrasts by subtraction between the images obtained under the two TIs; and
classifying the 7-12 months old into the third group, and setting TI to 600-700 ms during the 3D T1-weighted magnetic resonance imaging scans.

\* \* \* \* \*